(12) United States Patent
Lauber

(10) Patent No.: US 11,150,248 B2
(45) Date of Patent: Oct. 19, 2021

(54) METHODS FOR THE RAPID PREPARATION OF LABELED GLYCOSYLAMINES FROM COMPLEX MATRICES USING MOLECULAR WEIGHT CUT OFF FILTRATION AND ON-FILTER DEGLYCOSYLATION

(71) Applicant: WATERS TECHNOLOGIES CORPORATION, Milford, MA (US)

(72) Inventor: Matthew A. Lauber, North Smithfield, RI (US)

(73) Assignee: Waters Technologies Corporation, Milford, MA (US)

(*) Notice: Subject to any disclaimer, the term of this patent is extended or adjusted under 35 U.S.C. 154(b) by 58 days.

(21) Appl. No.: 16/314,554

(22) PCT Filed: Jun. 19, 2017

(86) PCT No.: PCT/US2017/038072
§ 371 (c)(1),
(2) Date: Dec. 31, 2018

(87) PCT Pub. No.: WO2018/005139
PCT Pub. Date: Jan. 4, 2018

(65) Prior Publication Data
US 2019/0170761 A1    Jun. 6, 2019

Related U.S. Application Data

(60) Provisional application No. 62/357,552, filed on Jul. 1, 2016.

(51) Int. Cl.
*G01N 33/68* (2006.01)
*C07K 1/13* (2006.01)
(Continued)

(52) U.S. Cl.
CPC ....... *G01N 33/6842* (2013.01); *B01D 15/305* (2013.01); *B01D 63/16* (2013.01);
(Continued)

(58) Field of Classification Search
CPC ........ B01D 15/305; B01D 63/16; C07K 1/13; C07K 1/36; G01N 1/28; G01N 1/4044;
(Continued)

(56) References Cited

U.S. PATENT DOCUMENTS 2,016,962 A    10/1935   Flint
4,003,912 A    1/1977    Franz
(Continued)

FOREIGN PATENT DOCUMENTS

CN    1211622 A    3/1999
CN    1973047 A    5/2007
(Continued)

OTHER PUBLICATIONS

Hirai, "Development of a new fluorescence labeling reagent succinimido-2-fluorenylcarbamate for highly sensitive detection of N-solanesyl-N,N-bis(3,4-dimethoxybenzyl) ethanediamine by HPLC," Anal. Chem. 1991, 40(5), 233-238. Abstract.
(Continued)

*Primary Examiner* — Jennifer Wecker
(74) *Attorney, Agent, or Firm* — Kacvinsky Daisak Bluni PLLC

(57) ABSTRACT

Methods for preparing labeled glycosylamines from a complex matrix are provided. The methodology includes the steps of: denaturing glycoproteins in a complex matrix to form a denatured complex matrix mixture; loading the denatured complex matrix mixture onto a MWCO filtration device; adding a glycosidase enzymatic solution onto the MWCO filtration device to form a deglycosylated complex matrix mixture comprising glycosylamines; collecting gly-
(Continued)

Figure 1:
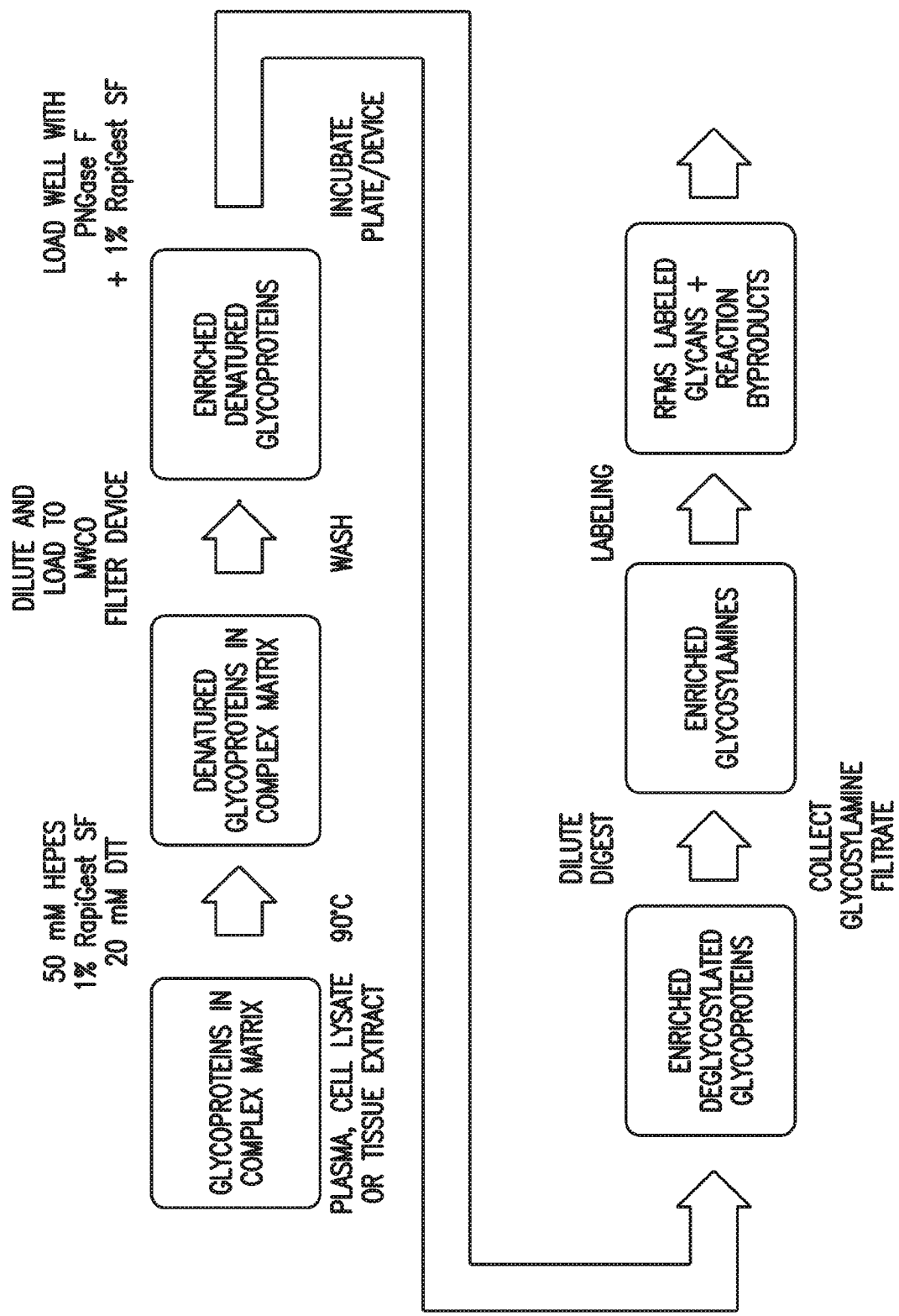

cosylamines released from the MWCO filtration device; and derivatizing glycosylamines with a rapid tagging reagent to form a plurality of labeled glycosylamines suitable for detection in various liquid chromatography systems and detectors.

16 Claims, 3 Drawing Sheets

(51) Int. Cl.
    *C07K 1/36*     (2006.01)
    *G01N 1/40*     (2006.01)
    *G01N 1/28*     (2006.01)
    *G01N 30/06*     (2006.01)
    *G01N 30/78*     (2006.01)
    *G01N 30/02*     (2006.01)
    *B01D 15/30*     (2006.01)
    *B01D 63/16*     (2006.01)

(52) U.S. Cl.
    CPC .................. *C07K 1/13* (2013.01); *C07K 1/36* (2013.01); *G01N 1/28* (2013.01); *G01N 1/4077* (2013.01); *G01N 30/06* (2013.01); *G01N 30/78* (2013.01); *G01N 1/4044* (2013.01); *G01N 2001/4088* (2013.01); *G01N 2030/027* (2013.01); *G01N 2030/067* (2013.01)

(58) Field of Classification Search
    CPC ......... G01N 1/4077; G01N 2001/4088; G01N 2030/027; G01N 2030/067; G01N 30/06; G01N 30/78; G01N 33/6842
    See application file for complete search history.

(56) References Cited

U.S. PATENT DOCUMENTS

| | | | |
|---|---|---|---|
| 4,068,528 A | 1/1978 | Gundelfinger | |
| 4,138,398 A | 2/1979 | Richter et al. | |
| 5,296,599 A | 3/1994 | Cohen et al. | |
| 5,531,959 A | 7/1996 | Johnson et al. | |
| 6,245,478 B1 | 6/2001 | Uetani et al. | |
| 6,379,971 B1 | 4/2002 | Schneider et al. | |
| 6,632,629 B2 | 10/2003 | Yang et al. | |
| 6,716,634 B1 | 4/2004 | Myerson | |
| 7,074,570 B2 | 7/2006 | Palmgren et al. | |
| 7,148,069 B2 | 12/2006 | Miyano et al. | |
| 7,186,739 B2 | 3/2007 | Guichard et al. | |
| 7,494,815 B2 | 2/2009 | Shimbo et al. | |
| 7,732,378 B2 | 6/2010 | Thompson et al. | |
| 8,124,792 B2 | 2/2012 | Baginski | |
| 8,198,063 B1 | 6/2012 | Baginski et al. | |
| 8,445,292 B2 | 5/2013 | Baginski | |
| 9,658,234 B2 | 5/2017 | Miyano et al. | |
| 10,416,166 B2 | 9/2019 | Brousmiche et al. | |
| 2001/0026929 A1 | 10/2001 | Yang et al. | |
| 2004/0259262 A1 | 12/2004 | Ishii | |
| 2005/0079624 A1 | 4/2005 | Miyano et al. | |
| 2005/0158708 A1 | 7/2005 | Alroy et al. | |
| 2005/0221337 A1 | 10/2005 | Seeberger et al. | |
| 2006/0004220 A1 | 1/2006 | Hamprecht et al. | |
| 2006/0035304 A1 | 2/2006 | Lebrilla et al. | |
| 2006/0127950 A1* | 6/2006 | Bosques ................ G01N 33/66 435/7.1 |
| 2006/0286673 A1 | 12/2006 | Miyano et al. | |
| 2007/0141723 A1 | 6/2007 | Sompuram et al. | |
| 2007/0269895 A1 | 11/2007 | Aebersold et al. | |
| 2008/0201095 A1 | 8/2008 | Yip et al. | |
| 2008/0241856 A1 | 10/2008 | Wong et al. | |
| 2008/0315084 A1 | 12/2008 | Yamada et al. | |
| 2009/0050212 A1 | 2/2009 | Dourdeville et al. | |
| 2009/0065687 A1 | 3/2009 | Gross et al. | |
| 2009/0258437 A1 | 10/2009 | Baginski | |
| 2010/0151499 A1 | 6/2010 | Collins et al. | |
| 2010/0171055 A1 | 7/2010 | Dourdeville | |
| 2011/0006237 A1 | 1/2011 | Tower | |
| 2011/0171736 A1 | 7/2011 | Agnew et al. | |
| 2012/0107942 A1 | 5/2012 | Baginski | |
| 2012/0165370 A1 | 6/2012 | Tang et al. | |
| 2013/0112604 A1 | 5/2013 | Keene et al. | |
| 2013/0171658 A1 | 7/2013 | Fulton et al. | |
| 2014/0030732 A1 | 1/2014 | Staples | |
| 2014/0038215 A1 | 2/2014 | Smart et al. | |
| 2014/0178912 A1 | 6/2014 | Liu et al. | |
| 2014/0179011 A1 | 6/2014 | Brousmiche et al. | |
| 2014/0200148 A1 | 7/2014 | Slade | |
| 2014/0227793 A1 | 8/2014 | Gao et al. | |
| 2014/0242709 A1 | 8/2014 | Brousmiche et al. | |
| 2014/0274768 A1 | 9/2014 | Haab | |
| 2014/0350263 A1 | 11/2014 | Brousmiche et al. | |
| 2014/0370614 A1 | 12/2014 | Liu et al. | |
| 2015/0057243 A1* | 2/2015 | Zhou ................ C12Q 1/48 514/45 |
| 2015/0204824 A1 | 7/2015 | Lauber et al. | |
| 2015/0346194 A1 | 12/2015 | Magnelli et al. | |
| 2016/0018409 A1 | 1/2016 | Higel | |
| 2016/0054274 A1 | 2/2016 | Cormier et al. | |
| 2016/0069844 A1 | 3/2016 | Jackson et al. | |
| 2016/0139136 A1 | 5/2016 | Brousmiche et al. | |
| 2017/0370813 A1* | 12/2017 | Steen ................ B01D 65/02 |

FOREIGN PATENT DOCUMENTS

| | | | |
|---|---|---|---|
| CN | 102690833 A | 9/2012 | |
| CN | 103918055 A | 7/2014 | |
| EP | 0671401 A1 | 9/1995 | |
| EP | 2305692 A1 | 4/2011 | |
| EP | 2990401 A1 | 3/2016 | |
| JP | S59161355 A | 9/1984 | |
| JP | S60186502 A | 9/1985 | |
| JP | S62195361 A | 8/1987 | |
| JP | H09101310 A | 4/1997 | |
| JP | H10306075 A | 11/1998 | |
| JP | H1180107 A | 3/1999 | |
| JP | 2000510854 A | 8/2000 | |
| JP | 2000329744 A | 11/2000 | |
| JP | 2001526048 A | 12/2001 | |
| JP | 2006038674 A | 2/2006 | |
| JP | 2012512234 A | 5/2012 | |
| JP | 2015091953 A | 5/2015 | |
| WO | 9921580 A1 | 5/1999 | |
| WO | 02074245 A2 | 9/2002 | |
| WO | 2004027388 A2 | 4/2004 | |
| WO | 2004086050 A2 | 10/2004 | |
| WO | 2006114663 A1 | 11/2006 | |
| WO | 2009070233 A1 | 6/2009 | |
| WO | 2011038873 A1 | 4/2011 | |
| WO | 2011146594 A2 | 11/2011 | |
| WO | 2013081581 A1 | 6/2013 | |
| WO | 2013084236 A1 | 6/2013 | |
| WO | 2013151975 A1 | 10/2013 | |
| WO | 2013192530 A2 | 12/2013 | |
| WO | WO-2013192530 A2 * | 12/2013 | ............... C12Q 1/34 |
| WO | 2014085938 A1 | 6/2014 | |
| WO | 2014194320 A1 | 12/2014 | |
| WO | 2016009077 A1 | 1/2016 | |
| WO | 2016069764 A1 | 5/2016 | |
| WO | WO-2016069764 A1 * | 5/2016 | ......... G01N 33/6842 |
| WO | 2016089515 A1 | 6/2016 | |

OTHER PUBLICATIONS

Hochleitner, E.O., et al., "Determination of the Stoichiometry of Protein Complexes Using Liquid Chromatography with Fluorescence and Mass Spectrometric Detection of Fluorescently Labeled Proteolytic Peptides", Proteomics 4:669-676 (2004).

Hossler et al., "Optimal and Consistent Protein Glycosylation in Mammalian Cell Culture", Glycobiology 19(9):936-949 (2009).

HP Primer Hewlett Packard, Basics of LC/MS: A Primer. 1998.

(56) References Cited

OTHER PUBLICATIONS

International Preliminary Report on Patentability, for International Application No. PCT/US2012/057996, dated Apr. 1, 2014, 5 pages.
International Search Report and Written Opinion for International App. No. PCT/US15/57848, dated Feb. 5, 2016, 5 pages.
International Search Report and Written Opinion for International Application No. PCT/US17/038073, dated Sep. 12, 2017, 9 pages.
International Search Report and Written Opinion for International Application No. PCT/US2017/038070, dated Sep. 29, 2017, 10 pages.
International Search Report and Written Opinion for International Application No. PCT/US2017/038072, dated Oct. 3, 2017, 9 pages.
International Search Report and Written Opinion for PCT/GB2016/051605 dated Sep. 15, 2016.
International Search Report and Written Opinion for International Application No. PCT/US2017/014790, dated Apr. 27, 2017, 7 pages.
International Search Report and Written Opinion, for International application No. PCT/US15/60326, dated Feb. 2, 2016, 6 pages.
International Search Report and Written Opinion, for International application No. PCT/US2012/057996 dated Jan. 31, 2013, 8 pages.
Isbell, H.S. et al., "Effect of pH in the Mutarotation and Hydrolysis of Glycosylamines", JAGS letter to editor, 72:1043-1044 (1950).
Iwaki, "Activated carbamate reagent as chiral derivatizing agent for liquid chromatographic optical resolution of enantiomeric amino compounds," Chromatographia 23(12):899-902 (1987) Abstract.
Iwaki, "Amino acid analysis by reversed-phase high-performance liquid chromatography automatic pre-column derivatization with activated carbamate reagent," Journal of Chromatography, 407:273-279 (1987) Abstract.
Jupille, "UV-Visible Absorption Derivatization in iquid Chromatography," Journal of Chromatographic Science 1979, 17(3):160-167. Abstract.
Keough, "Atmospheric Pressure Matrix-Assisted Laser Desorption/Ionization Ion Trap Mass Spectrometry of Sulfonic Acid Derivatized Tryptic Peptides," Rapid Communications in Mass Spectrometry 15(23):2227-2239 (1987) Abstract.
Kimzey, Michael et al., "Development of an Instant Glycan Labeling Dye for High Throughput Analysis by Mass Spectrometry", Prozyme Advancing Glycosciences, May 13, 2015, 4 pages.
Kinzel, O., et al., "Identification of MK-5710 ((8aS)-8a-methyl-1,3-dioxo-2-(1S,2R)-2-phenylcyclopropyl]-N-(1-phenyl-1H-pyrazol-5-yl)hexahydro-imidazo [1,5-a]pyrazine-7(1 H)-carboxamide), a potent smoothened antagonist for use in Hedgehog pathway dependent malignancies, Part 2", Bioorganic & Medicinal Chemistry Letters 21:4429-4435 (2011).
Klapoetke, S, et al., "The Evaluation of a Novel Approach for the Profiling and Identification of N-linked Glycans With a Procainamide Tag by HPLC With Fluorescent and Mass Spectrometric Detection", Journal of Pharmaceutical and Biomedical Analysis 53(3):315-324 (2010).
Knezevic, A., et al., "High throughput plasma N-glycome profiling using multiplexed labelling and UPLC with fluorescence detection", Analyst, 136:4670 (2011).
Kuster, B., et al: "Structural Determination of N-linked carbohyrdrates by matrix-assisted laser desorption/ionization-mass spectrometry following enzymatic release within sodium dodecyl sulphate-polyacrylamide electrophoresis gels: application to species-specific glycosylat", Electrophoresis: Liquid Phase Separation Techniques: Microfulidics, Naoanalysis, Proteomics, Wiley Interscience, DE, vol. 19, No. 11, pp. 1950-1959, Aug. 1, 1998.
Kurita, K., et al., "Synthesis and Properties of Polyurethanes Derived from Bis-N-Hydroxyimides and Diisocyanates", Journal of Polymer Science 17:1619-1629 (1979).
Lauber et al., Optimization of GlycoWorks HILIC SPE for the Quantitative and Robust Recovery of N-Linked Glycans from mAb-Type Samples. Waters Application Note (2013) 9 pages.
Cline et al., "The Aminolysis of N-Hydroxysuccinimide Esters. A Structure-Reactivity Study", J Am Chem Soc 109(10):3087-3091 (1987).

Lawrence, "Derivatization in Chromatography Introduction, Practical Aspects of Chemical Derivatization in Chromatography," Journal of Chromatographic Science 17(3):113-114 (1979) Abstract.
Li De et al.,"Techniques of Biomolecule Scientific Experiments", Hunan Science and Technology Press, Nov. 2001, the 1st edition, p. 32-33.
Liu et al., Investigation of Sample Preparation Artifacts Formed during the Enzymatic Release of N-Linked Glycans prior to Analysis by Capillary Electrophoresis. Anal. Chem. 81: 6823-6829 (2009).
Liu, H., et al., "Determination of Submicromolar Concentrations of Neurotransmitter Amino Acids by Fluorescence Detection Using a Modification of the 6-Aminoquinolyl-N-Hydroxysuccinimidyl Carbamate Method for Amino Acid Analysis", Journal of Chromatograpjy A, 828:383-395 (1998).
Liu, H., et al., "Femtomole Peptide Mapping by Derivatization, High-Performance Liquid Chromatography, and Fluorescence Detection", Analytical Biochemistry 294(1):7-18 (2001) Abstract.
Liu, Hongji, et.al.; "Homogeneous Fluorescent Derivatization of Large Proteins", Journal of Chromatography A, 927(10-2): 77-89 (2001) Abstract.
Louris, "New Scan Modes Accessed with a Hybrid Mass Spectrometer," Anal. Chem. 57(14):2916-2924 (1985) Abstract.
Ma, "Determination of Midazolam and its Metabolites in Serum Microsamples by High-Performance Liquid Chromatography and its Application to Pharmacokineics in Rats," J Chromatography B Biomed Appl. 682(1):109-113. (1996) Abstract.
Marino et al., "A Systematic Approach to Protein Glycosylation Analysis: A Path Through the Maze", Nature Chemical Biology 6:713-723 (2010) Abstract.
Martinez-Force, E., et al., "Separation of O-Phthalaldehyde Derivatives of Amino Acids of the Internal Pool of Yeast by Reverse-Phase Liquid Chromatography", Biotechnology Technique 5(3):209-214 (1991).
Mazzocchi, Paul et al., "A Photochemical Route to Pyrrolo[1,4]Benzodiazepine Antitumor Antibiotics" Heterocycles 23(7):1603-1606 (1985).
McLafferty, "Interpretation of Mass Spectra," Fourth Edition, University Science Books, Sausalito, CA 1993, Chapter 1. Abstract.
Mechref et al., Quantitative Glycomics Strategies, Mol Cell Proteomics 12 (4):874-84 (2013).
Morpugo, "N-hydroxysuccinimide carbonates and carbamates are useful reactive reagents for coupling ligands to lysines on proteins," J. Biochem. Biophys. Methods 38:17-28 (1999).
Nakashima, "Study on $\pi$-$\pi$ Interaction in High Performance Liquid Chromatography," J. Liq. Chrom. Rel. Technol. 23(16):2533-2540 (2000) Abstract.
Nimura, "Detection reagent for high performance liquid chromatography," Pharmacia 17(8):707-709 (1981).
Nimura, N., et al., "Activated Carbamate Reagent as Derivatizing Agent for Amino Compounds in High-Performance Liquid Chromatography", Analytical Chemistry 58(12):2372-2375 (1986).
Okamoto, "Sensitive Detection and Structural Characterization of Trimethyl(p-aminophenyl)-ammonium-derivatized Oligosaccharides by Electrospray Ionization-Mass Spectrometry and Tandem Mass Spectrometry," Rapid Communications in Mass Spectrometry, 9:641-643. (1995) Abstract.
Pall Life Sciences "AcroPrep Advance Filter Plates" Pall Corporation (Mar. 2013) p. 7, col. 2, 10 Table AcroPrep Advance 96—Well Filter Plates for Ultrafiltration.
Park, S., et al., "Regioselective Covalent Modification of Hemoglobin in Search of Antisickling Agents", J Med Chem 46(6):936-953 (2003) Abstract.
Chalmers, "Advances in Mass Spectrometry for Proteome Analysis," Current Opinion in Biotechnology 11(4): 384-390 (2000) Abstract.
Pettersson et al., Chemical Stability of Reversed Phase High Performance Liquid Chromatography Silica under Sodium Hydroxide Regeneration Conditions, J Chromatogr A 1142 (1 ): 93-7 (2000).
Piepponen, T.P., et al., Rapid and Sensitive Step Gradient Assays of Glutamate, Glycine, Taurine and y-Aminobutyric Acid by High-Performance Liquid Chromatography-Fluorescence Detection with

(56) References Cited

OTHER PUBLICATIONS o-Phthalaldehyde-Mercaptoethanol Derivatization With an Emphasis on Microdialysis Samples, Journal of Chromatography B, 757:277-283 (2001).
PUBCHEM CID: 43450869 2-N-[3-(Diethylamino)propyl] quinoline-2,6-diamine, Create Date: Jul. 21, 2009.
EP12836127.6 Opposition Communication Jul. 23, 2019. 10 pages.
Ahn J., et al., "Separation of 2-aminobenzamide labeled glycans using hydrophilic interaction chromatography columns packed with 1. 7 μm sorbent," Journal of Chromatography B, 878:403-8 (2010).
Anumula et al., "High Resolution and High Sensitivity Methods for Oligosaccharide Mapping and Characterization by Normal Phase High Performance Liquid Chromatography Following Derivitization with Highly Flourescent Anthranilic Acid", Glycobiology 8(7):685-694 (1998).
Bartlet-Jones, "Peptide ladder sequencing by mass spectrometry using a novel, volatile degradation reagent," Rapid Commun. Mass Spectrom. 8(9):737-742 (1994) Abstract.
Bereman et al., Increasing the hydrophobicity and electrospray response of glycans through derivatization with novel cationic hydrazides, Chem Commun (Camb) 46(2): 237-9 (2010).
Black, S.D., et al., "Simple, Rapid, and Highly Efficient Separation of Amino Acid Phenylthiohydantoins by Reversed-Phase High-Performance Liquid Chromatography", Analytical Biochemestry 121:281-285 (1982).
Block et al., "2050P: HPLC/MS Analysis of Amino Acids: The Use of 6-Aminoquinolyl-N-Hydroxy-Succinimidyl Carbamate Derivatives", Poster presented at Pittsburgh Conference, Mar. 1999.
Block, E., et al., "2050P: HPLC-MS Analysis of Amino Acids", Abstract presented at Pittsburgh Conference, Mar. 1999.
Block, E.H., "LC/MS Application Notes: The Use of 6-Aminoquinolyl N Hydroxy Succinimidyl Carbamate Derivatives for HPLC/MS Analysis of Amino Acids", Presentation at Pittsburgh Conference, Mar. 1999.
Summons to attend oral proceedings pursuant to Rule 115(1) EPC for Application No. EP15180680.9, dated Jul. 18, 2019, 4 pages.
Summons to attend oral proceedings pursuant to Rule 115(1) EPC for Application No. EP15180680.9, dated Jun. 17, 2019, 9 pages.
Vollhardt, "Organic Chemistry Structure and Function," Third Edition, W. H. Freeman and Company, 1999, Chapters 14, 20, 21, 26. Abstract.
Wada, Y., et al., "Comparison of the Methods For Profiling Glycoprotein Glycans—HUPO Human Disease Glycomics/Proteome Initiative Multi-Institutional Study", Glycobiology 17(4):411-422 (2007).
Walker et al., Hydrophobic Derivatization of N-linked Glycans for Increased Ion Abundance in Electrospray onization Mass Spectrometry, J Am Soc Mass Spectrom 22(8):1309-17 (2011).
Waters Corporation "GlycoWorks High-Throughput Sample Preparation Kit" (Sep. 2013).
CNOA for application 201580071764.2 dated Feb. 28, 2020 original and translated document, 18 pages.
Fu-Chuan, Li, et al., "Studies on Fluorescent Labeling of Marine Sulfated Polysaccharide 911", Chemical Journal of Chinese Universities, 23(9):1704-1708 (2002).
Zailin, W., "Studies on Fluorescent Labeling of Several Fungal Polysaccharides", Chinese Masters Thesis, Agriculture Science and Technology, original and translated document, No. 5 (2013).
Takeda, K., et al., Convenient Methods for Syntheses of Active Carbamates, Ureas and Nitrosoureas Using N,N'-Disuccinimido Carbonate (DSC), Tetrahedron Letters 24(42):4569-72 (1983) Abstract.
Tarentino, A.L., et al., "2-Iminothiolane: A Reagent for the Introduction of Sylphydryl Groups into Oligosaccharides Derived from Asparagine-Linked Glycans", Glycobiology 3(3):279-285 (1993) (Abstract).
Tousi "The Pursuit of Cancer Biomarkers: Liquid Chromatography and Mass Spectrometry 1-13, Platforms for Glycomic Characterization of Biospecimens" Northeastern University, Jul. 16, 2013.
Ciucanu et al., A Simple and Rapid Method for the Permethylation of Carbohyrates, Carbohydr. Res. 131:209-217 (1984).

Ullmer, R., et.al., "Derivatization by 6-aminoquinolyl-N-hydroxysuccinimidyl Carbamate for Enhancing the ionization Yield of Small Peptides and Glycopeptides in Matrix-Assisted Laser Desorption/Ionization and Electrospray ionization Mass Spectrometry", Rapid Communications in Mass Spectrometry 20:1469-1479 (2006).
Voet, "Biochemistry" Second Edition, John Wiley Sons, Inc. 1995, Chapters 4, 5. Abstract.
Van Wandelen, C., et al., "Using Quaternary High-Performance Liquid Chromatography Eluent Systems for Separating 6-Aminoquinolyl-N-Hydroxysuccinimidyl Carbamate-Derivatized Amino Acid Mixtures", Journal of Chromatography A, 763:11-22 (1997).
Vasilevich, N., et al., "Conversion of O-Succinimidyl Carbamates to N-(O-Carbamoyl)-Succinmonoamides and Ureas: Effects of N-Substituents and Reaction Conditions on the Reaction Pathway", Tetrahedron Letters 43(37):6649-6652 (2002) Abstract.
Watson, "Introduction to Mass Spectrometry" Raven Press, New York 1985, Chapters 1 and 4. Abstract.
Wei, W.-J., et al., "Study on N-Hydroxyphthalimide as Blocking Agent for Isocyanates", Journal of Applied Polymer Science 84:1346-1352 (2002).
Wuhrer, M., et al., "Nano-Scale Liquid Chromatography-Mass Spectrometry of 2-Aminobenzamide-Labeled Oligosaccharides at Low Femtomole Sensitivity", International Journal of Mass Spectrometry 232:51-57 (2004).
Yates, et al. "Peptide Mass Maps: A Highly Informative Approach to Protein Identification," Analytical Biochemistry 214:397-408 (1993).
Yodoshi, M., et al: "Optimized conditions for high-perfonmance liquid chromatography analysis of oligosaccharides using 7-amino-4-methylcoumarin as a reductive amination reagent", Journal of Chromatography A 1203 (2):137-145 (2008).
Yost, RA and Enke, CG, "Triple Quadrupole Mass Spectrometry for Direct Mixture Analysis and Structure Elucidation," Analytical Chemistry 51(12):1251A-1264A (1979) Abstract.
Yu Y. Q., "N-linked Glycan Characterization and Profiling: Combining the Power of Accurate Mass, Reference Glucose Units, and UNIFI Software for Confident Glycan Assignments," Waters, Application Note (2013) 10 pages.
Yu Y.Q., et al., "A Rapid Sample Preparation Method for Mass Spectrometric Characterization of N-linked Glycans", Rapid Communications in Mass Spectrometry 19:2331-2336 (2005).
Zhang Li et al., "Practical Guidance of Detection by Separation", Press of University of Science and Technology of China, Jan. 2013, p. 55.
Chapter 2—Norepinephrine (NPL cited during EP3472132 examination procedure) Jul. 16, 2020.
Yang et al., "Solid-phase glycan isolation for glycomics analysis", Proteomics Clin Appl. 6(0): 596-608. (Year: 2012).
Johannesen et al. "Glycan analysis via derivatization with a fluorogenic pyrylium dye", Carbohydrate Research, vol. 352(1):94-100 (Year: 2012) Abstract.
Extended European Search Report for Application No. EP20188814.6, dated Oct. 2, 2020, 7 pages.
Block, E.H., "The Use of 6-Aminoquinolyl-N-Hydroxy Succinimidyl Carbamate Derivatives for HPLC/MS Analysis of Amino Acids", AMD35 Waters Alliance LC/MS System 2000.
Brancia, "Improved matrix-assisted laser desorption/ionization mass spectrometric analysis of tryptic hydrosylates of proteins following guanidation of lysine-containing peptides," Rapid Commun. Mass Spectrom. 14(21):2070-2073 (2000) Abstract.
Briggs, J.B., et al., "An analytical system for the characterization of highly heterogeneous mixtures of N-linked oligosacchandes", Analytical Biochemistry, 389:40-51 (2009).
Brophy, JJ et al., "Electron Impact and chemical ionization mass spectra of aryl ureas," Organic Mass Spectrometry, 14(7):379-386 (1979) Abstract.
Buku, A., et al., "2,3-trans-3,4-trans-3,4-Dihydroxy-L-proline: An Amino Acid in Toxic Peptides of *Amanita virosa* Mushrooms," Proc. Natl. Acad. Sci. USA 77(5): 2370-2371 (1980).

(56) References Cited

OTHER PUBLICATIONS

Bunz, S-C., et al., "Analysis of native and APTS-labeled N-glycans by capillary electrophoresis/time-of-flight mass spectrometry", Analytical and Bioanalytical Chemistry 405:8277-8284 (2013).
Busto, "Solid phase extraction of biogenic amines from wine before chromatographic analysis of their AQC derivatives," J. Liq. Chrom. & Rel. Technol. 20(5):743-755 (1997) Abstract.
Byrnes, PJ et al., "6-Aminoquinoline as a Fluorogenic Leaving Group in Peptide Reactions: A New Fluorogenic Substrate for Chymotrypsin," Anal. Biochem. 116(2):408-413 (1981) Abstract.
Campbell M. P., et al., "GlycoBase and autoGU: tools for HPLC-based glycan analysis," Bioinformatics, 24(9):1214-1216, (2008).
Casoli, A., et al., "Use of High-Performance Liquid Chromatography For the Determination of Amino Acids in Sparkling Wines", Am J Enol Vitic 33(3):135-139 (1982).
Cech and Enke, "Relating Electrospray Ionization Response to Nonpolar Character of Small Peptides," Anal. Chem. 72(13):2717-2723 (2000) Abstract.
Extended European Search Report for Application No. EP17820918.5, dated Jan. 28, 2020, 7 pages.
Paschinger, K., et al., "Analysis of zwitterionic and anionic N-linked glycans from invertebrates and protists by mass spectrometry", Glycoconjugate Journal, 33(3):273-283 (2016).
Qu, Y., et al., "Structural analysis of N- and O-glycans using ZIC-HILIC/dialysis coupled to NMR detection", Fungal Genetics and Biology, 72:207-215 (2014).
Lauber, M.A., et al., "Rapid Preparation of Released N-Glycans for HILIC Analysis Using a Labeling Reagent that Facilitates Sensitive Fluorescence and ESI-MS Detection", Analytical Chemistry, 87(10):5401-5409 (2015).
Author unknown, Best Practices in the Analysis of Rapifluor-MS Labeled Glycans Using the Acquity QDa Detector (Performance Model), Waters [online] Mar. 2016 White Paper [retrieved on Apr. 1, 2020]. Retrieved from the Internet URL: https://www.gimitec.com/file/720005655en.pdf, 19 pages.
Amendment dated Sep. 9, 2011 and response in U.S. Appl. No. 12/365,880.
Decision on Rejection, Chinese Application No. 201280047599.3, dated Dec. 5, 2016, Original and translated.
Extended European Search Report and Written Opinion for EP Application No. 15855907.0 dated Mar. 19, 2018, 10 pages.
European Search Report and Written Opinion dated Feb. 2, 2016 regarding patent application No. EP 15180680.9, 7 pages.
Expert Declaration by Prof. Ulf Diederichsen submitted in the opposition proceedings relating to the European patent EP2761296B1, dated Jul. 23, 2019, 7 pp.
Extended European Search Report for Application No. 17767589.9, dated Jan. 30, 2020, 11 pages.
Extended European Search Report for EP Application No. 17815987.7, dated Dec. 16, 2019, 8 pages.
Extended European Search Report, EP 12836127.6, Aug. 26, 2014.
Fekkes, "State-Of-The-Art of High-Performance Liquid Chromatographic Analysis of Amino Acids in Physiological Samples," Journal of Chromatography B. 682(1):3-22 (1996).
Field, B., et al, Chromatography Forum: LC-MS & GC-MS Archives: AAA LC-MS [online] 2003 [retrieved on Jan. 30, 2003]. Retrieved from Internet URL: http://www. lcresources. com/d iscus/messages/5135/3143. html, 6 pages.
GlykoPrep™ Instant AB now fully commercialized [online] Mar. 2011 [retrieved on Sep. 13, 2020]. Retrieved from Internet URL: web.archive.org/web/20120115033552/http://www.europa-bioproducts.com/latest/aspx?id=14.
Gong et al., "N-Glycosylamine-Mediated Isotope Labeling for Mass Spectrometry-Based Quantitative Analysis of N-linked Glycans", Anal Bioanal Chem 405:5825-31 (2013).
Guichard, G., et al., "Effective Preparation of O-Succinimidyl-2-(tert-Butoxycarbonylamino)ethylcarbamate Derivatives from Beta-Amino Acids. Application to the Synthesis of Urea-Containing Pseudopeptides and Oligoureas", Journal of Org Chem 64:8702-8705 (1999).

Guile G. R., et al., "A Rapid High-Resolution High-Performance Liquid Chromatographic Method for Separating Glycan Mixtures and Analyzing Oligosaccharide Profiles," Analytical Biochemistry, 240: 210-226, (1996).
West, C., et al., "Porous Graphitic Carbon: a Versatile Stationary Phase for Liquid Chromatography", J Chromatogr A 1217(19):3201-16 (2010).
H. R. Liang, et al., "Quantitative determination of endogenous sorbitol and fructose in human nerve tissues by atmospheric-pressure chemical ionization liquid chromatography tandem mass spectrometry", Rapid Communications in Mass Spectrometry, 19(16):2284-2294 (2005) Abstract.
Harvey, D.J., "Electrospray Mass Spectrometry and Fragmentation of N-Linked Carbohydrates Derivatized at the Reducing Terminus", J Am Soc Mass Spectrom 11(10):900-15 (2000).
Harvey, et al., "Proposal for a standard system for drawing structural diagrams of N- and O-linked carbohydrates and related compounds", Proteomics 9(15): 3796-801 (2009).
Harvey, D., "Identification of protein-bound carbohydrates by mass spectrometry" Proteomics 1:311-328 (2001).
Heindel, N.D., et al., "Diaminoquinoline antimalarials", J. Med. Chem. 12(5):797-801 (1969).
Heinze-Krauss, I., et al., "Structure-Based Design of B-Lactamase Inhibitors. 1. Synthesis and Evaluation of Bridged Monobactams", Journal of Med Chem 41(21):3961-3971 (1998) Abstract.
Hermanson, "Bioconjugate Techniques," 1996, Chapter 8. Abstract.
Higashi, T., et al., "Derivatization of Neutral Steroids to Enhance Their Detection Characteristics in Liquid Chromatography-Mass Spectrometry", Anal Bioanal Chem 378:875-882 (2004).
Higuchi, K., et al., "Chemistry of Succinimido Esters. IV*1. A Facile Preparation of N-Succinimidyl Carboxylates Using N, N'-Disuccinimidyl Carbonate", Oil Chemistry, 36(1):16-20 (1987).
Registry File from STN for compound RN 1915940-97-4, entered on STN May 23, 2016, downloaded Sep. 8, 2020 (Year: 2016).
Registry File from STN for compound RN 1919202-16-6, entered on STN May 27, 2016, downloaded Sep. 8, 2020 (Year: 2016).
Registry File from STN for compound RN 1970079-84-5, entered on STN Aug. 9, 2016, downloaded Sep. 8, 2020 (Year: 2016).
Registry File from STN for compound RN 1975675-34-3, entered on STN Aug. 19, 2016, downloaded Sep. 8, 2020 (Year: 2016).
Registry File from STN for compound RN 1977407-60-5, entered on STN Aug. 22, 2016, downloaded Sep. 8, 2020 (Year: 2016).
Notice for Reasons for Rejection, dated Jul. 23, 2012, In Japanese Application No. 2009-269796 original document and translation.
Harvey, D.J., "Derivatization of carbohydrates for analysis by chromatography: electrophoresis and mass spectrometry", Journal of Chromatography B 879(17-18):1196-1225 (2010). Abstract.
Non-Final Office Action, U.S. Appl. No. 14/193,418, dated Nov. 15, 2016.
Non-Final Office Action, U.S. Appl. No. 14/342,131, dated Nov. 4, 2016.
Notice of Rejection, JP Application No. 2014-533416, dated Jan. 10, 2017. Original and Translated.
Office Action, U.S. Appl. No. 14/458,760, dated Apr. 12, 2017.
Response to EP Communication with extended search report, EP Application No. 15180680.9, dated Sep. 2, 2016.
Response to Non-Final Office Action, U.S. Appl. No. 14/342,131 dated Feb. 6, 2017.
Response to Non-Final Office Action, U.S. Appl. No. 14/193,418, dated Feb. 15, 2017.
Response to notice of opposition for EP Patent No. 2761296 filed Oct. 19, 2018.
Response to Office Action, U.S. Appl. No. 14/458,760, dated Jun. 12, 2017.
Response to Restriction Requirement, U.S. Appl. No. 14/342,131 dated Sep. 28, 2016.
Restriction Requirement, U.S. Appl. No. 14/342,131, dated Aug. 17, 2016.
Communication pursuant to Article 94(3) EPC, for Application No. EP17820918.5, dated Nov. 26, 2020, 5 pages.
Neville, D.C.A., et al., "Development of a Single Column Method for the Separation of Lipid- and Protein-Derived Oligosaccharides", Journal of Proteome Research, 8(2):681-687 (2009).

(56) References Cited

OTHER PUBLICATIONS

Comunication pursuant to Article 94(3) EPC in European Patent Application No. 17815987.7, dated Dec. 4, 2020, 5 pages.
Cohen, SA, et al., "Clearing the Hurdle of High Sensitivity in Biopharmaceutical Research," LC GC North America 17(4S): S9-S16 (1999).
Cohen, S. A., et al.,"Compositional Protein Analysis Using 6-Aminoquinolyl-N-Hydroxysuccinimidyl Carbamate, a Novel Derivatization Reagent", Techniques in Protein Chemistry IV pp. 289-298 (1993).
Cohen, S. A., et al., "Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography", Analytical Biochemistry 211:279-87 (1993).
Communication of a notice of opposition for EP Patent No. 2761296 mailed Jun. 5, 2018.
Communication pursuant to Article 94(3) EPC for Application No. EP17188121.2, dated Sep. 14, 2020, 3 pages.
Communication pursuant to Article 94(3) EPC, dated Apr. 17, 2019, for Application No. EP15855907.0, 4 pages.
Cook et al., Development and Qualification of An Antibody Rapid Deglycosylation Method, Biologicals 40(2):109-17 (2012).
Cooper, D., et al., "LC-MS/MS Analysis of AccQ-Tag Derivatised Amino Acids", Micromass UK Limited pp. 1-7 (2000).
Cooper, D., et al., "LC-MS/MS Analysis of AccQ-Tag Derivatised Amino Acids, Micromass Application Brief", Sep. 2000 and Jun. 2000.
Cooper, D., et al., "LC-MS-MS Analysis of Amino Acids Using AccQ-Tag derivatisation, Application Brief AB25", Micromass Jun. and Sep. 2000.
Covey, "Liquid Chromatography/Mass Spectrometry," Analytical Chemistry 58(14):1451A-1461A (1986) Abstract.
Dextran Calibration Ladder Standard. Waters (2012), 3 pages.
Darren L. Holmes, Eric M. Smith, and James S. Nowick "Solid-Phase Synthesis of Artificial beta-Sheets" Journal of American Chemical Society 119: 7665-7669 (1997).
De Antonis, K. M., et al., "High-Performance Liquid Chromatographic Analysis of Synthetic Peptides Using Derivatization with 6-Aminoquinolyl-N-Hydroxysuccinimidyl Carbamate", Analytical Biochemistry 223:191-197 (1994).
De Hoffmann, "Mass Spectrometry, Principles and Applications," Second Edition, John Wiley Sons Ltd. 2001, Introduction, Chapters 1, 3, and 7. Abstract.
De Hoffmann, "Tandem Mass Spectrometry: A Primer," J. Mass Spec. 31(2):129-137 (1996 ) Abstract.
Dell, "Fast Atom Bombardment Mass Spectrometric Strategies for Characterizing Carbohydrate-containing Biopolymers," Biomedical and Environmental Mass Spectrometry, 16(1-12):19-24 (1988) Abstract.
Dextran Calibration Ladder. Waters. Product Solution (2013) 3 pages.
Chezal, J-M., et al. "Evaluation of Radiolabeled (Hetero)Aromatic Analogues of N-(2-diethylaminoethyl)-4-iodobenzamide for Imaging and Targeted Radionuclide Therapy of Melanoma" J. Med. Chem. 51:3133-3144 (2008).
Quirke, "Chemical Derivatization for Electrospray Ionization Mass Spectrometry. 1. Alkyl Halides, Alcohols, Phenols, Thiols, and Amines" Anal Chem. 66(8):1302-1315 (1994) Abstract.
Rasmussen, "The nomenclature of fused-ring arenes and heterocycles: a guide to an increasingly important dialect of organic chemistry," ChemTexts, 2(16):1-13 (2016).
Reubsaet, "Characterisation of π-π interactions which determine retention of aromatic compounds in reversed-phase liquid chromatography," Journal of Chromatography A, 841(2):147-154 (1999) Abstract.
Extended European Search Report for Application No. 15855907.0, dated Jul. 6, 2018 , 12 pages.
EP Communication pursuant to Article 94(3) EPC, EP Application No. 12836127.6, dated Sep. 26, 2016.

EP Communication under Rule 71(3) EPC, EP Application No. 12836127.6, dated Mar. 15, 2017.
EP Communication with extended search report, EP Application No. 15180680.9, dated Feb. 2, 2016.
European Search Report and Written Opinion dated Aug. 26, 2014 regarding patent application No. EP12836127.6.
Roth, "Charge Derivatization of Peptides For Analysis By Mass Spectrometry," Mass Spectrometry Reviews 17(4):255-274 (1998) Abstract.
Rudd, "Rapid, sensitive sequencing of oligosaccharides from glycoproteins," Current Opinion in Biotechnology x 8:488-497 (1998).
Ruhaak et al. Glycan Labeling Strategies and their use in Identification and Qualification, Anal Bioanal Chem x 397(8):3457-3481(2010).
Saurina, J., et al., "Chromatographic Determination of Amino Acids by Pre-Column Derivatization Using 1,2-Napthoquinone-4-Sulfonate As Reagent", Journal of Chromatography A, 740:21-30 (1996).
Saurina, J., et al., "Determination of Amino Acids by Ion-Pair Liquid Chromatography With Post-Column Derivatization Using 1,2-Naphthoquinone-4-Sulfonate", Journal of Chromatography A, 676:311-319 (1994).
Schmeer, K., et al., "Compositional Analysis of the Phenylthiocarbamyl Amino Acids by Liquid Chromatography-Atmospheric Pressure Ionization Mass Spectrometry with Particular Attention to the Cyst(e)ine Derivatives", Journal of Chromatography A, 691:285-299 (1995).
Schmidt, C.J., et al., "Amino Acid Profiling of Protein Hydrolysates Using Liquid Chromatography and Fluorescence Detection", Journal of Liquid Chromatography 2(7):1031-1045 (1979).
Schwartz, "Multistage mass spectrometry: Scan modes and new instrumentation" Dissertation 1989.
Schwartz, "Systematic Delineation of Scan Modes in Multidimensional Mass Spectrometry," Anal. Chem. 62(17)1809-1818 (1990) Abstract.
Schwartz, B., et al., "A Kinetic Characterization of the Glycosyltransferase Activity of *Eschericia coli* PBP1b and Development of a Continuous Fluorescence Assay", Biochemistry, 41:12552-12561 (2002).
Search Report for GB1509402.2 dated Mar. 4, 2016.
Shimbo, "Multifunctional and Highly Sensitive Precolumn Reagents for Amino Acids in Liquid Chromatography/Tandem Mass Spectrometry," Anal. Chem. 81(13):5172-5179 (2009) Abstract.
Snyder, "Introduction to Modern Liquid Chromatography," Second Edition, John Wiley & Sons, Inc. 1979, Introduction, Chapters 2, 4, 13, 14, 17. Abstract.
Synder, "Practical HPLC Method Development," Second Edition, John Wiley & Sons, Inc. 1997, Chapters 3, 4. Abstract.
Song, X., et al., "Glycan microarrays off fluorescently-tagged natural lycans" Glycoconjugate Journal, 32:465-473 (2015).
Spengler, "Peptide sequencing of charged derivatives by postsource decay MALDI mass spectrometry," Int. J. Mass Spectrom. Ion Processes x69/170:127-140 (1990) Abstract.
Statement of grounds appeal for European patent application No. 15180680.9, dated May 20, 2020, 4 pages.
Stockmann, "Ultrahigh Throughput, Ultrafiltration-Based NGlycomics Platform for Ultraperformance Liquid Chromatography (ULTRA3)," Anal. Chem. 87(16):8316-8322 (2015) Abstract.
Struwe et al. Aminoquinolines as fluorescent labels for hydrophilic interaction liquid chromatography of oligosaccharides, Biological Chemistry, 393:757-765 (2012).
Supplementary European Search Report, EP12836127.6 dated Sep. 12, 2014 and Response dated Mar. 19, 2015.
Suzuki,et al, "Comparision of the Sensitivities of Various Derivatives of Oligosacchardies in LC/MS with Fast Atom Bombardment and Elecgtrospray Ionization Interfaces", Analytical Chemistry 68(13):2073-2083 (1996).
Bioengineering Analysis and Inspection, (pp. 162-163) Wang Furong China Light Industry Press pub. Jun. 30, 2005.
Cosgrave, E and McCarthy,. M Investigation of the Factors that Contribute to Glycan Separation in HI LIC, Businness Operations, Pharmaceutical Life Sciences, Waters Corporation (Year: 2014).

(56) References Cited

OTHER PUBLICATIONS

CNOA for Patent Application No. 201780053453.2 dated Feb. 4, 2021, original and translated document 24 pages.
Zhang, Y., ed., Biological Sample Library Establishment and Practice, p. 102 Sun Yat-Sen University Press (Oct. 2013).
Huang, R., ed., Analytical Chemistry, National Defense Science and Technology University Press pp. 146-150 (Mar. 2014).

* cited by examiner

METHODS FOR THE RAPID PREPARATION OF LABELED GLYCOSYLAMINES FROM COMPLEX MATRICES USING MOLECULAR WEIGHT CUT OFF FILTRATION AND ON-FILTER DEGLYCOSYLATION

CROSS-REFERENCE TO RELATED APPLICATIONS

This application is a national phase filing claiming the benefit of and priority to International Patent Application No. PCT/US2017/038072, filed on Jun. 19, 2017, which claims priority to U.S. Provisional Patent Application No. 62/357,552 filed Jul. 1, 2016, incorporated herein by reference.

BACKGROUND

Methods for analyzing a glycoprotein present in a complex matrix include the steps of deglycosylation followed by derivatization with a labeling reagent to produce derivatized glycosylamines. Under certain conditions, derivatization can be performed without separation of the glycoprotein from a biological sample. In given instances, the analysis of derivatized glycosylamines in a complex matrix can continue through to the analysis and/or detection including high performance liquid chromatography ("HPLC"), ultra-high performance liquid chromatography (UHPLC), mass spectrometry ("MS"), supercritical fluid chromatography, ultraviolet ("UV"), fluorescent ("FLR") detection, matrix assisted laser desorption ionization mass spectrometry ("MALDI-MS") and/or capillary electrophoresis ("CE").

Furthermore, methods have been recently developed that permit rapid derivatization of glycosylamines without causing degradation of the biological sample or over-labeling. One such procedure has been described where sample is deglycosylated, without prior purification, and subjected to labeling with a rapid tagging reagent, RapiFluor-MS ("RFMS"). See, International Application No. PCT/US2015/057848, published as WO 2016/069764. However, not all sample types are amenable to this minimalistic approach as they might contain nucleophilic molecules capable of interfering with the glycosylamine derivatization reaction.

In such cases, glycoproteins often require the use of detergents and other reagents for effective solubilization. These detergents and reagents must be removed before mass spectrometric detection as the presence of which can be detrimental to the analysis. Moreover, a large number of cells might be required, prohibiting medium to high-throughput analysis and often precluding production of replicates, resulting in an inability to report the differences between the inherent sample-to-sample variability and variances between distinct biological samples. Rahman, S. A, et al., *Filter-Aided N-Glycan Separation (FANGS): A Convenient Sample Preparation Method for Mass Spectrometric N-Glycan Profiling*, J. Proteome Res. 2014, 13, 1167-1176 (2014) at 1167-68.

As such, methodologies have been developed to overcome these issues and can include the use of methyl-esterified sialic acids, expensive reagents such as siRNA, and/or isolated membranes—none of which are suitable solutions for medium to high throughput analysis. Id. at 68. Furthermore, the glycosylamine isolation and purification steps of the methods can be elaborate, particularly for a mass spectrometric analysis. Id. Moreover, methods have been designed to immobilize glycoprotein onto membranes. The membranes, however, are constructed of hydrophobic polymers, such as PVDF, nylon and nitrocellulose, and are limited in binding capacity because such membranes rely upon adsorption based retention. See e.g., Baginski et al., U.S. Pat. No. 8,198,063 B 1. For example, at increasingly higher mass loads, the hydrophobic membrane will become saturated. Also, non-analyte, hydrophobic compounds will foul the hydrophobic membrane to the point that adsorption of glycoproteins to the membrane is outcompeted.

A need exists, therefore, for methods that can establish a medium to high throughput analysis of glycosylamines from complex matrices.

SUMMARY

Methods for preparing labeled glycosylamines from a complex matrix are provided. The present methods comprise the steps of: (a) denaturing glycoproteins in a complex matrix to form a denatured complex matrix mixture; (b) loading the denatured complex matrix mixture onto a molecular weight cut off ("MWCO") filtration device; (c) adding a glycosidase enzymatic solution onto the MWCO filtration device, wherein the glycoproteins on the MWCO filtration device are deglycosylated and form a deglycosylated complex matrix mixture comprising glycosylamines; (d) collecting glycosylamines released from the MWCO filtration device; and (e) derivatizing glycosylamines with a rapid tagging reagent to form a plurality of labeled glycosylamines. In an embodiment, the method can further comprise the step of diluting the denatured complex matrix mixture. In an embodiment, the method can further comprise a step of centrifuging the denatured complex matrix mixture. Furthermore, in an embodiment the method can also comprise the step of diluting the deglycosylated complex matrix mixture. In an embodiment, the MWCO filtration device is heated and/or incubated. In an embodiment, the MWCO filtration device is a 96-well filter plate. In an embodiment, the glycosylamines flow through the MWCO filtration device to a filtrate collection device. In an embodiment, the plurality of labeled glycosylamines are detected in a liquid chromatography system.

Also, provided herein is a kit for preparing glycosylamines comprising a MWCO filtration device, a rapid tagging reagent, a denaturing solution and an enzymatic solution. The denaturing solution denatures glycoproteins in a complex matrix to form a denatured complex matrix mixture. The enzymatic solution is mixed and incubated with the denatured complex matrix on the filtration device to yield glycosylamines. The deglycosylated complex matrix mixture is subjected to filtration with a MWCO filtration device to yield glycosylamines. The glycosylamines are derivatized with a rapid tagging reagent. The labeled glycosylamines are detectable in liquid chromatography systems, capillary electrophoresis and/or MALDI-MS systems. Further provided herein is a liquid chromatography system having a MWCO filtration device, a fluorescence detection device and a mass spectrometric detection device. In the liquid chromatography system, the MWCO filtration device is configured to produce glycosylamines which are collected for derivatization and subsequent fluorescence detection in the fluorescence detection device and mass spectrometric detection in the mass spectrometric detection device.

DETAILED DESCRIPTION OF THE DRAWINGS

FIG. 1 is a schematic of the method steps for the preparation of labeled glycosylamines from complex matrices using on-filter deglycosylation.

Figure 2A:
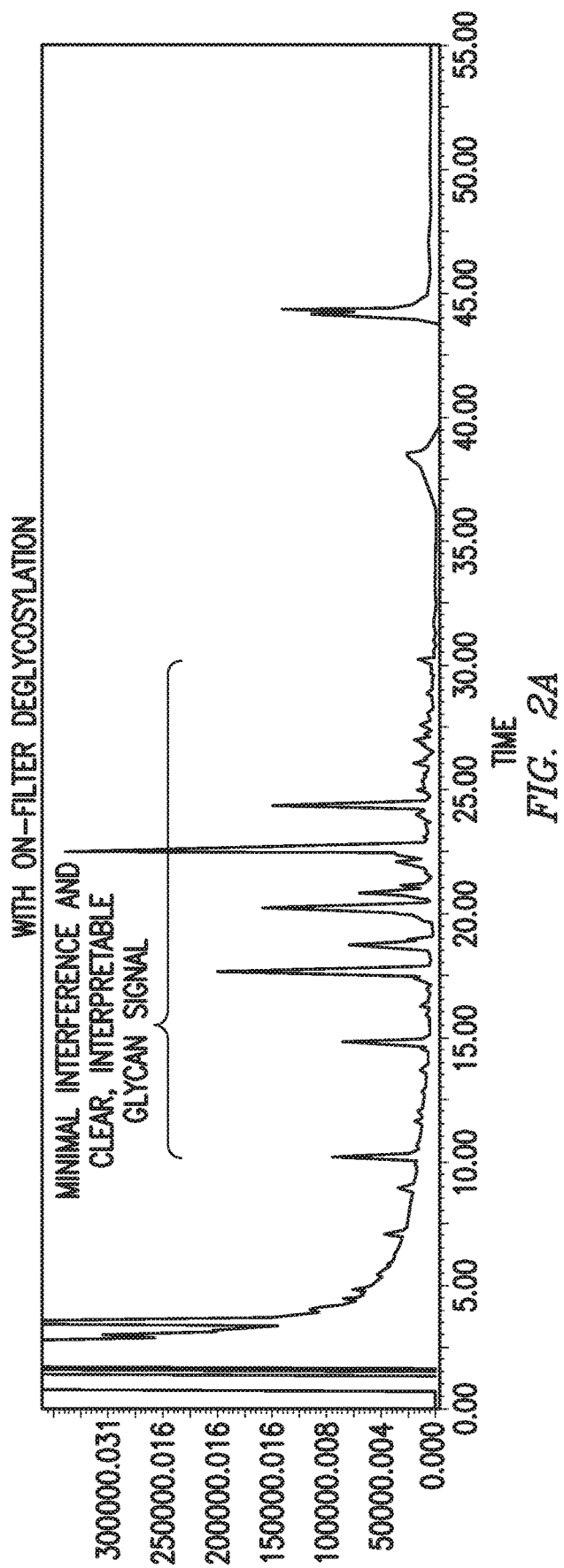
Figure 2B:
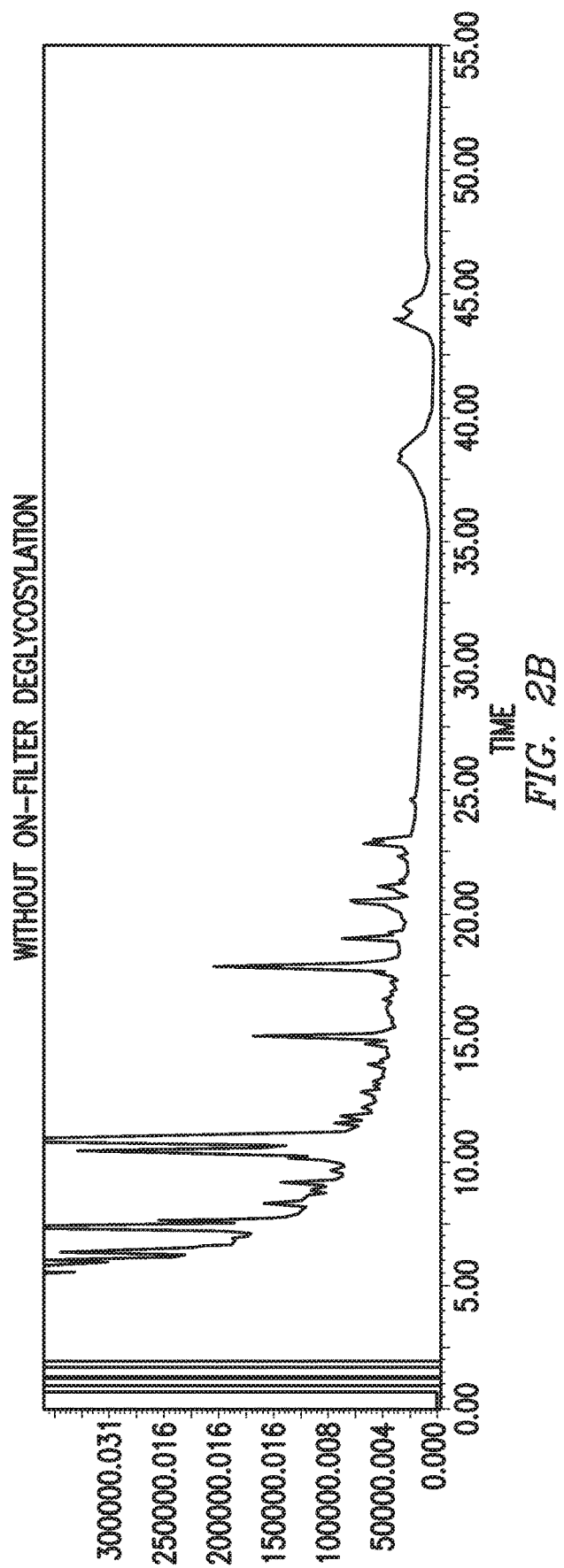

FIGS. 2A and 2B show a comparison of labeled glycosylamine sample as analyzed by hydrophilic interaction chromatography and fluorescence detection. FIG. 2A shows clear, interpretable glycan signal as a result of performing a sample preparation with on-filter deglycosylation. FIG. 2B shows compromised glycan signal as a result of performing a sample preparation without on-filter deglycosylation.

DETAILED DESCRIPTION

Described herein is a novel approach for the preparation of labeled glycosylamines from complex matrices, generally referred to as "on-filter deglycosylation." Glycosylamines, or N-glycosides, are a class of compounds consisting of an amine with a β-N-glycosidic bond to a carbohydrate, forming a cyclic hemiaminal ether bond (α-aminoether). Glycosylamines have a glycosyl group attached to an amino group. Glycosylamines can include, but are not limited to, nucleosides such as adenosine, and glycosides with an amine group such as N,N-dimethyl-β-D-glucopyranosylamine, glucosylamine, glucosyl-n-butylamine, glucosyl-n-hexylamine, glucosyl-n-octylamine, glucosyl-n-decylamine, glucosyl-n-dodecylamine, maltosyl-n-dodecylamine. D-glucose, D-galactose, lactose, cellobiose, and maltose will all yield corresponding glycosylamines, 1-amino-1-deoxy-D-glucose, 1-amino-1-deoxy-D-galactose, 1-amino-1-deoxylactose, 1-amino-1-deoxycellobiose and 1-amino-1-deoxymaltose, upon treatment with aqueous solution of ammonia in the presence of one equivalent of ammonium hydrogen carbonate.

We have discovered that not all complex matrices (also referred to herein as "glycoprotein samples" or "samples") are amenable to preparation techniques previously described. See e.g., Lauber, M. A. et al, *Rapid Preparation of Released N-Glycans for HILIC Analysis Using a Labeling Reagent that Facilitates Sensitive Fluorescence and ESI-MS Detection. Anal Chem*, 87 (10), 5401-9 (2015). Certain glycoprotein analytes are contained in complex matrices that may include, among other things, nucleophilic molecules which are capable of interfering with a glycosylamine derivatization reaction.

Therefore, presented herein are methodologies for preparing labeled glycosylamines from complex matrices. In the present methods, the glycoprotein sample is deglycosylated on a molecular weight cut off ("MWCO") filtration device to minimize both the number of sample handling steps and the sample preparation time. After the deglycosylation reaction, glycosylamines are filtered through the MWCO filter and the resulting glycosylamine filtrate is derivatized with reagent. The derivatized glycosylamines are then subjected to analysis using high performance liquid chromatography ("HPLC"), ultra-high performance liquid chromatography (UHPLC), mass spectrometry ("MS"), supercritical fluid chromatography, ultraviolet ("UV"), matrix assisted laser desorption ionization mass spectrometry ("MALDI-MS"), capillary electrophoresis ("CE"), and/or fluorescent ("FLR") detection.

The term, glycoprotein is a polypeptide that is modified with a saccharide.

The term, complex matrix, or in the plural complex matrices, means and includes, but is not limited to, plasma, cellular lysates, biofluids and/or tissue extracts.

Glycosylation is a posttranslational modification of secreted and membrane proteins. Different monosaccharides are linked to each other to form oligosaccharides and one or more of the resulting glycan chains may be attached to the polypeptide backbone to form a glycoprotein. Hence, certain glycosylamines (such as glycans) are important modulators of protein function but have functions of their own in cell/tissue structure and signaling. Rahman, S. A, et al., *Filter-Aided N-Glycan Separation (FANGS): A Convenient Sample Preparation Method for Mass Spectrometric N-Glycan Profiling, J. Proteome Res.* 13, 1167-1176 (2014) at 1167.

An example preparation workflow for the present methods of preparing labeled glycosylamines from glycoproteins contained within complex matrices is shown in FIG. 1. In the present methods, labeled (or "tagged") glycosylamines are prepared from glycoproteins which are first denatured in the complex matrix. In a denaturation step, the complex matrix containing glycoprotein is mixed with a solution comprising a buffer, optionally a reducing agent (also referred to as a "redox reagent"), and surfactant and/or other reagents that enhance enzymatic digestion of protein, and subsequently heated to form a denatured complex matrix. The denatured complex matrix (containing denatured glycoprotein) can then be diluted. In the denaturation step, a certain amount of thiol reducing agent between about 1 to about 100 mM can be added to the complex matrix which is to the benefit of making glycans accessible for deglycosylation. The addition of thiol reducing agent cannot otherwise be incorporated without employing a filter assisted approach because a thiol is sufficiently nucleophilic to compete for the glycosylamine derivatization reagent. With the filter assisted approach, denatured glycoproteins in the complex matrix undergo a buffer exchange with a derivatization compatible buffer and are therefore concentrated. So while optional, dilution is preferred.

In an embodiment, to denature the glycoprotein in a complex matrix, a solution having a pH of 7.9 comprising 50 mM HEPES, 20 mM dithiothreitol ("DDT") and 1% RapiGest SF is mixed with lysate (the complex matrix) containing o.5 mg/ml of protein, forming a complex matrix mixture. RapiGest SF is a surfactant/reagent used to enhance enzymatic digestion of protein both in-gel and in-solution and solubilize protein making protein more susceptible to enzymatic cleavage without inhibiting enzyme activity. The complex matrix mixture is then heated at 90° C. for three minutes generating a denatured complex matrix mixture, and subsequently diluted with 270 µL of water to form a diluted denatured complex matrix mixture.

In an on-filter deglycosylation step, the denatured complex matrix mixture is then loaded onto a molecular weight cut off ("MWCO") filtration device. In an embodiment, the denatured complex matrix mixture is filtered and centrifuged, diluted with water and centrifuged again. More specifically, in an embodiment, the denatured complex matrix mixture is centrifuged for about six minutes, but can be centrifuged between about 1 minute and about 20 minutes.

Following dilution and centrifugation of the denatured complex matrix mixture, a glycosidase enzyme, such as PNGase F, is then added to the MWCO filtration device to form a deglycosylated complex matrix mixture. The glycosidase enzymatic solution may comprise non-nucleophilic buffer compounds, examples include, but are not limited to phosphate or HEPES buffered solutions. In addition, other buffering zwitterionic compounds, like HEPES, and having a pKa between about 7 to about 9 that are non-nucleophilic may be used in an enzymatic deglycosylation solution including, but not limited to, ADA (N-(2-Acetamido)-2-iminodiacetic acid), BES (N,N-Bis(2-hydroxyethyl)-2-aminoethanesulfonic acid), BICINE (N,N-Bis(2-hydroxyethyl) glycine), DIPSO (3-(N,N-Bis[2-hydroxyethyl]amino)-2- hydroxypropanesulfonic acid), EPPS (4-(2-Hydroxyethyl)-1-piperazinepropanesulfonic acid), HEPBS (N-(2-Hydroxyethyl)piperazine-N'-(4-butanesulfonic acid)), MOBS (4-(N-Morpholino)butanesulfonic acid), MOPS (3-(N-Morpholino)propanesulfonic acid), MOPSO (3-(N-Morpholinyl)-2-hydroxypropanesulfonic acid), PIPES (1,4-Piperazinediethanesulfonic acid), POPSO (Piperazine-N,N'-bis(2-hydroxypropanesulfonic acid)). An ionization state of the buffering compound being neutral or positive, rather than negative, may further reduce the chromatographic background. Therefore, cationic, non-nucleophilic buffer compounds, such as tertiary amines: TEA (triethylammonia), BIS-TRIS (2,2-Bis(hydroxymethyl)-2,2',2''-nitrilotriethanol), BIS-TRIS propane (1,3-Bis[tris(hydroxymethyl)methylamino]propane) may be used.

Basic enzymatic deglycosylation of glycoproteins utilize glycosidases including, but not limited to, N-glycosidase A (PNGase A), N-glycosidase F (PNGase F), O-glycosidase, Neuraminidase, β1-4 Galactosidase and β-N-Acetylglucosaminidase. For example, as described in detail herein, glycoprotein samples can be deglycosylated with the enzyme, peptide N-glycosidase F (PNGase F), that removes N-linked oligosaccharides from glycoproteins, except for compounds containing α(1-3)-linked fucose on the reducing terminal. N-glycosidase A (PNGase A) can remove all N-glycans, however. Other useful enzymes include endoglycosidases or glycoamidases such as endoglycosidase and N-glycanase. Upon enzymatic deglycosylation, N-glycans are released from asparagines residue as glycosylamines.

Thereafter, the MWCO filtration device can be incubated and/or heated so as to catalyze the release of glycosylamines. The MWCO device can be heated between about 30° C. to about 70° C. for a period of time between about 1 minute to about 60 minutes.

The MWCO filtration device useful in connection with the present methods can be constructed from many different designs, ranging from single cartridges to 96-well plates to capillary tube formats. In an embodiment, a 96-well MWCO plate such as that provided by the Pall Life Sciences AcroPrep™ Advance 96 Filter Plate part number 8164 or 8034 can be used. This filter plate is designed to bind proteins and nucleic acids and is useful in biomolecule recovery. Single cartridge devices could likewise be used such as Millipore Amicon Ultra-0.5 mL centrifugal filters.

In practice, the MWCO filtration device can have flow driven through it by a multitude of mechanisms, among them centrifugation, vacuum and positive pressure. The incubation of the MWCO filtration device can also be accomplished via different means, including convection heating in an oven and direct heating applied to the device itself. MWCO filtration devices can have different properties and be made of different materials. Often a filtration membrane is manufactured to have pore properties that will result in the retention of certain solute sizes. For instance, a 10 kDa MWCO filtration membrane is manufactured so as to show retention of compounds weighing 10 kDa. Species larger than 10 kDa will be more efficiently retained, while species smaller than 10 kDa will more readily filter through the material. In an embodiment, a 10 kDa MWCO filtration device was selected, as it will facilitate the retention of most proteins, yet allow the passage of glycosylamines. The average molecular weight of a protein from a eukaryotic organism is approximately 60 kDa, while the molecular weight of N-glycosylamines ranges from 1 to 6 kDa. A 10 kDa MWCO filtration device is accordingly suited to the sample preparation technique. Nevertheless, it is foreseeable that either lower or higher cut-offs could be used, for instance 3 kDa or 30 kDa MWCO filters. In addition, the MWCO filtration device can be constructed of varying materials including, but not limited to, polyether sulfone ("PES") and regenerated cellulose.

The on-filter deglycosylation step may also take place on a device like that described by Kim et al., in which a chromatographic system is used to drive continuous flow through a microbore hollow fiber enzyme reactor. Here, glycoprotein and enzyme is retained by the microbore hollow fiber enzyme reactor. Kim, J. Y., et al., *Development of an Online Microbore Hollow Fiber Enzyme Reactor Coupled with Nanoflow Liquid Chromatography-Tandem Mass Spectrometry for Global Proteomics*, Analytical Chemistry, (85), 5506-5513 (2013). As deglycosylation of protein can take place in the on-filter deglycosylation step, released glycosylamines filter through the MWCO fiber to a downstream vessel in which labeling can be carried out.

Noteworthy is the fact that the MWCO filtration devices described herein are not faced with the issues described above related to an on-membrane deglycosylation, with hydrophobic membrane s discussed above because filtration depends on a size exclusion mechanism and not adsorption. As such, the ability to load protein on the MWCO filtration device is comparatively higher. In addition, unlike a hydrophobic membrane, a MWCO filter device is not fouled by hydrophobic compounds.

Upon completion of the deglycosylation reaction, glycosylamines are filtered through the MWCO filtration device and the protein counterparts are retained in a filtrate collection step. Thereby, the glycosylamines are removed from the sample to produce a deglycosylation mixture. In the filtrate collection step, the deglycosylation complex matrix mixture can be diluted, and centrifuged. The filtrate containing glycosylamines (or "glycosylamine containing filtrate") is then derivatized with a rapid tagging reagent such as those described in U.S. patent application Ser. No. 14/458,760 (published as US2014/0350263) at ¶¶ [0008]-[0022], [0054]-[182] and [0191], and Ser. No. 15/005,619 (published as US2016-0139136) at page 2, line 20 through page 4, line 10, incorporated by reference.

The present methods can be carried out by a liquid handling system (referred to sometimes as a "liquid handling robot" or "liquid handling workstation"). The liquid handling systems are useful to automate laboratories. In the liquid handling system, a robot dispenses a selected quantity of reagent, samples or other liquid to a designated container. In an embodiment, the liquid handling system dispenses an allotted volume of liquid from a motorized pipette or syringe. Other more complicated machines can also manipulate the position of the dispensers and containers (often a Cartesian coordinate robot) and/or integrate additional laboratory devices, such as centrifuges, microplate readers, heat sealers, heater/shakers, bar code readers, spectrophotometric devices, storage devices and incubators. More complex liquid handling workstations can perform multiple tasks such as sample transport, sample mixing, manipulation and incubation, as well as transporting vessels to/from other workstations. Hence, liquid handling systems can be as simple as a bench-top 8-channel DNA PCR processing robot or range to a customized-for-process automated liquid handling system.

Conditions of the labeling reaction, including temperature, organic solvent composition, organic solvent concentration, buffer composition, pH, ionic strength, molar excess of reagent, and time are selected and controlled such that desired reaction selectivity between primary amines and hydroxyl groups is achieved. In turn, the yield of labeled glycans is optimized and the generation of so-called "over-labeled" glycans (glycans/glycosylamines modified by >1 label) is minimized. An optional quenching solution can comprise a hydrophilic amine containing compound. Ethylene diamine can also be used. This quenching solution not only controls the time a glycosylamine is allowed to react with the labeling reagent, but also shifts the pH of the reaction to an elevated pH (>10), which enhances the solubility of the labeled glycans in high organic solvents (i.e. >50% acetonitrile), and thereby facilitating downstream SPE procedures based on hydrophilic interaction chromatography ("HILIC").

In an embodiment, high labeling yields of derivatized compounds can be achieved with minimal levels of over labeling when: (1) temperature is at ambient to sub-ambient temperatures; (2) dimethylformamide (DMF) is used as an organic solvent; (3) DMF comprises no more than 20-30% of the reaction mixture; (4) a sodium phosphate solution buffer between pH 7.9 and pH 8.2 is employed, and (5) a phosphate concentration is maintained at ≤50 mM. Here, over labeling is anticipated to be less than about 1 mole percent, more preferably about 0.0 to about 0.5 mole percent, and about 0.0 to about 0.2 percent. In addition, the buffer concentration can be between about 5 mM to about 1000 mM, or in some embodiments about 5 mM to about 200 mM or about 5 mM to about 100 mM or about 5 mM to 50 mM. A high yield of labeled glycosylamines can be achieved having a molar excess of the labeling reagent over modifiable amine in an amount ranging between about 10 to about 2000, or about 30 to about 1000, or about 40 to about 500; or about 50 to about 300. Previously, we discovered that 20-30% DMF is sufficient to enhance solubility without significantly impacting the yield and selectivity of the labeling reaction. For this reason, a reaction mixture comprised of 20-30% DMF is preferred.

Derivatized glycosylamines are then analyzed using liquid chromatography and/or other detection methods and systems including, but not limited to, high performance liquid chromatography (HPLC), ultra-high performance liquid chromatography (UHPLC), mass spectrometry ("MS"), supercritical fluid chromatography, ultraviolet ("UV") and/or fluorescent ("FLR") detection, and/or with analytical instrumentation such as capillary electrophoresis ("CE"), high-performance anion-exchange chromatography with pulsed amperometric detection ("HPAEC-PAD"), hydrophilic interaction chromatography-liquid chromatography with fluorescence detection ("HILIC-LC/FLR"), reverse phase liquid chromatography mass spectrometry ("RPLC/MS"), and matrix-assisted laser desorption/ionization mass spectrometry.

Unlike prior art methods, in present methods, proteinaceous amines and interfering nucleophiles are depleted from the sample. Therefore, it is anticipated that less labeling reagent is needed. Also, by using this sample preparation, labeled glycosylamines are readily obtained from complex matrices that present clear, interpretable signal on analytical testing platforms, such as hydrophilic interaction chromatography paired with fluorescence or mass spectrometric detection (FIG. 2).

Example I

HeLa cell lysate (Abcam ab170197) was subjected to a rapid tagging methodology for labeled glycosylamines via the use of on-filter deglycosylation. HeLa cell lysate was mixed and brought to 0.5 mg/mL protein concentration in a 30 μL volume comprised of 50 mM HEPES, pH 7.9, 1% (w/v) RapiGest SF, 20 mM dithiothrietol (DTT). The mixture was heated at 90° C. for 3 minutes then diluted with 270 μL of water to form a diluted denatured complex matrix mixture. This diluted, denatured complex matrix mixture was then transferred to a 10 kDa MWCO filter device (Pall Life Sciences AcroPrep™ Advance 96 Filter Plate part number 8164) and centrifuged at 4,000 g for 6 minutes. The filtered concentrate was next diluted with 300 μL of water and again centrifuged at 4,000 g for 6 minutes. Onto the collected concentrate and the filter membrane, a 20 μL PNGase F solution was dispensed (50 milli IUB/mL PNGase F (New England BioLabs P0709) in 50 mM HEPES, 1% (w/v) RapiGest SF pH 7.9). The MWCO filter device was next heated by a convection oven such that the deglycosylation mixture was incubated at an average temperature of 50° C. across 15 minutes. After incubation, the deglycosylation mixture was diluted with 20 μL of water and filtrate was collected from the MWCO filter device via centrifugation at 4,000 g for 3 min. This filtrate, containing released glycosylamines, was then subjected to a derivatization reaction, wherein the approximately 60 μL aqueous filtrate was mixed with 16 μL of 27.2 mg/mL RapiFluor-MS solubilized anhydrous dimethylformamide (DMF). After 5 minutes, the resulting labeled glycosylamines were prepared for analysis by dilution with an additional 17 μL of DMF and 70 μL of acetonitrile.

Glycosylamines from the above mentioned preparations were analyzed by hydrophilic interaction chromatography to compare their amenability to a ubiquitous released glycan analytical test. The following liquid chromatography ("LC") conditions were employed:

Column: Waters ACQUITY UPLC Glycan BEH Amide 130 Å 1.7 μm 2.1×50 mm
Mobile Phase A: 50 mM Ammonium Formate Buffer, pH 4.4
Mobile Phase B: Acetonitrile
Column Temperature: 60° C.
Injection Volume: 12.5-18 μL
Sample Concentration: The equivalent of approximately 0.1 mg/mL HeLa Cell Lysate protein
Fluorescence Detection: Ex 265 nm/Em 425 nm (2 Hz)

| Gradient Time Table | | | | |
| --- | --- | --- | --- | --- |
| Time | Flowrate | % A | % B | Curve |
| 0.0 | 0.4 | 25 | 75 | 6 |
| 35.0 | 0.4 | 46 | 54 | 6 |
| 36.5 | 0.2 | 100 | 0 | 6 |
| 39.5 | 0.2 | 100 | 0 | 6 |
| 43.1 | 0.2 | 25 | 75 | 6 |
| 47.6 | 0.4 | 25 | 75 | 6 |
| 55.0 | 0.4 | 25 | 75 | 6 |

For a comparison sample preparation, HeLa cell lysate was also prepared without on-filter deglycosylation, according to a previously described experimental procedure. Lauber, M. A. et al, *Rapid Preparation of Released N-Glycans for HILIC Analysis Using a Labeling Reagent that Facilitates Sensitive Fluorescence and ESI-MS Detection. Anal Chem*, 87 (10), 5401-9 (2015) except that there was a 15 minutes of incubation period for deglycosylation to account for convective versus direct heating, and four times lower concentration of RFMS was required to maintain optimal reagent excess that account for the fact that the filter preparation involves labeling of sample depleted of protein, and that DTT was used in the denaturation step.

Data corresponding to this comparison example are shown in FIG. 2, where it can be evidenced that the on-filter deglycosylation approach to rapidly preparing labeled glycosylamine facilitates obtaining cleaner, interpretable glycan signal when samples containing complex matrices are encountered.

I claim:

1. A method for preparing labeled glycosylamines from a complex matrix, comprising the steps of:
   denaturing glycoproteins in a complex matrix by mixing the complex matrix with a denaturing solution comprising a buffer and a surfactant and heating to form a denatured complex matrix mixture;
   diluting and loading the denatured complex matrix mixture onto a MWCO filtration device and filtering the denatured complex matrix mixture;
   subsequently adding a glycosidase enzymatic solution comprising a glycosidase enzyme and a non-nucleophilic buffer compound onto the MWCO filtration device, containing the diluted denatured complex matrix mixture, and incubating the MWCO filtration device wherein the glycoproteins on the MWCO filtration device are deglycosylated and form a deglycosylated complex matrix mixture comprising glycosylamines;
   collecting glycosylamines released from the MWCO filtration device; and
   derivatizing glycosylamines with a rapid tagging reagent to form a plurality of labeled glycosylamines.

2. The method of claim 1, wherein the MWCO filtration device is heated.

3. The method of claim 1, wherein the denatured complex matrix mixture is loaded onto the MWCO filtration device by a liquid handling system.

4. The method of claim 1, further comprising the step of centrifuging the denatured complex matrix mixture.

5. The method of claim 1, further comprising the step of diluting the deglycosylated complex matrix mixture.

6. The method of claim 1, wherein the glycosylamines flow through the MWCO filtration device to a filtrate collection device.

7. The method of claim 1, wherein the plurality of labeled glycosylamines are detected in a liquid chromatography system.

8. The method of claim 1, wherein the MWCO filtration device is a 96-well filter plate.

9. The method of claim 1, wherein the complex mixture is selected from plasma, cellular lysates, biofluids and/or tissue extracts.

10. The method of claim 1, wherein the non-nucleophilic buffer compound is a zwitterionic non-nucleophilic buffer compound and wherein the buffer compound has a pKa between about 7 and about 9.

11. The method of claim 1, wherein the non-nucleophilic buffer compound is a non-nucleophilic cationic buffer compound.

12. The method of claim 1, further comprising analyzing the plurality of labeled glycosylamines by mass spectrometric detection.

13. The method of claim 1, wherein the denaturing solution further comprises a thiol reducing agent in a concentration between 1 to 100 mM.

14. A method for preparing labeled glycosylamines from a complex matrix, comprising the steps of:
   denaturing glycoproteins in a complex matrix by mixing the complex matrix with a denaturing solution comprising a buffer, a thiol reducing agent in a concentration between 1 to 100 mM, and a surfactant and heating to form a denatured complex matrix mixture;
   diluting and loading the denatured complex matrix mixture onto a MWCO filtration device and filtering the denatured complex matrix mixture;
   subsequently adding a glycosidase enzymatic solution comprising a glycosidase enzyme and a non-nucleophilic zwitterionic buffer compound having a pKa between about 7 and about 9 or a non-nucleophilic cationic buffer compound onto the MWCO filtration device, containing the diluted denatured complex matrix mixture, and incubating the MWCO filtration device wherein the glycoproteins on the MWCO filtration device are deglycosylated and form a deglycosylated complex matrix mixture comprising glycosylamines;
   collecting glycosylamines released from the MWCO filtration device; and
   derivatizing glycosylamines with a rapid tagging reagent to form a plurality of labeled glycosylamines.

15. The method of claim 14, wherein the glycosidase enzymatic solution comprises the non-nucleophilic zwitterionic buffer compound having a pKa between about 7 and about 9.

16. The method of claim 14, wherein the non-nucleophilic cationic buffer compound.

* * * * *